(12) United States Patent
Kopper et al.

(10) Patent No.: US 10,504,295 B2
(45) Date of Patent: Dec. 10, 2019

(54) SYSTEMS AND METHODS FOR USING SENSING OF REAL OBJECT POSITION, TRAJECTORY, OR ATTITUDE TO ENABLE USER INTERACTION WITH A VIRTUAL OBJECT

(71) Applicant: Duke University, Durham, NC (US)

(72) Inventors: Regis Kopper, Durham, NC (US); Derek Nankivil, Durham, NC (US); David Zielinski, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/335,079

(22) PCT Filed: Sep. 27, 2017

(86) PCT No.: PCT/US2017/053803
§ 371 (c)(1),
(2) Date: Mar. 20, 2019

(87) PCT Pub. No.: WO2018/064213
PCT Pub. Date: Apr. 5, 2018

(65) Prior Publication Data
US 2019/0221043 A1    Jul. 18, 2019

Related U.S. Application Data

(60) Provisional application No. 62/400,124, filed on Sep. 27, 2016.

(51) Int. Cl.
*G06T 19/00*    (2011.01)
*G06F 3/01*    (2006.01)
(Continued)

(52) U.S. Cl.
CPC ............ *G06T 19/006* (2013.01); *G06F 3/011* (2013.01); *G06F 17/5009* (2013.01);
(Continued)

(58) Field of Classification Search
CPC ......... G06T 19/006; G06T 7/70; G06F 3/011; G06F 17/5009; G06K 9/00201
See application file for complete search history.

(56) References Cited

U.S. PATENT DOCUMENTS

2012/0113223 A1    5/2012    Hilliges et al.
2012/0206452 A1    8/2012    Geisner et al.
(Continued)

OTHER PUBLICATIONS

International Search Report and Written Opinion for PCT/US2017/053803 dated Dec. 4, 2017.
(Continued)

*Primary Examiner* — Ryan R Yang
(74) *Attorney, Agent, or Firm* — Olive Law Group, PLLC

(57) ABSTRACT

Systems and methods for using positions of detected, real object boundaries to enable user interaction with a virtual object are disclosed. A system can include one or more sensors or trackers configured to detect boundaries of a transparent, real object within a three-dimensional coordinate system. A computing device configured to track positions of the detected boundaries of the real object within the three-dimensional coordinate system. The computing device may also track a position of a virtual object within the three-dimensional coordinate system. The computing device may determine whether the position of the virtual object is within the positions of the detected boundaries of the real object. The computing device may also enable user interaction with the virtual object via user interface and receive input for interacting with the virtual object in response to determining that the position of the virtual object is within the positions of the detected boundaries.

40 Claims, 10 Drawing Sheets

(51) Int. Cl.
*G06T 7/70* (2017.01)
*G06F 17/50* (2006.01)
*G06K 9/00* (2006.01)
*G06T 15/00* (2011.01)
*G06T 15/20* (2011.01)

(52) U.S. Cl.
CPC ............ *G06K 9/00201* (2013.01); *G06T 7/70* (2017.01); *G06T 15/005* (2013.01); *G06T 15/20* (2013.01)

(56) References Cited

U.S. PATENT DOCUMENTS

| | | | |
|---|---|---|---|
| 2012/0250940 A1* | 10/2012 | Kasahara | G06F 3/011 382/103 |
| 2013/0286004 A1 | 10/2013 | McCulloch et al. | |
| 2015/0356788 A1* | 12/2015 | Abe | A63F 13/428 345/633 |
| 2016/0189426 A1 | 6/2016 | Thomas et al. | |

OTHER PUBLICATIONS

Eppel. "Tracing the boundaries of materials in transparent vessels using computer vision." In: arXiv preprint. Jan. 20, 2015. Retrieved from <file:///C:/Users/evely/Documents/Landon%20IP/17-53803,%20due%2011-13/EPPEL.pdf>.

International Preliminary Report on Patentability and Written Opinion issued in PCT Application No. PCT/US2017/053803 dated Apr. 12, 2019 (twelve (12) pages).

* cited by examiner

SYSTEMS AND METHODS FOR USING SENSING OF REAL OBJECT POSITION, TRAJECTORY, OR ATTITUDE TO ENABLE USER INTERACTION WITH A VIRTUAL OBJECT

CROSS REFERENCE TO RELATED APPLICATION

This is a 371 national stage patent application, which claims priority to PCT International Patent Application No. PCT/US2017/053803, filed Sep. 27, 2017, and titled SYSTEMS AND METHODS FOR USING SENSING OF REAL OBJECT POSITION, TRAJECTORY, OR ATTITUDE TO ENABLE USER INTERACTION WITH A VIRTUAL OBJECT, which claims priority to U.S. Provisional Patent Application No. 62/400,124, filed Sep. 27, 2016, and titled APPARATUS FOR THE TANGIBLE INTERACTION IN VIRTUAL AND MIXED REALITY SYSTEMS AND METHODS OF USING THE SAME, the disclosures of which are incorporated herein by reference in their entireties.

TECHNICAL FIELD

The presently disclosed subject matter relates to augmented and virtual reality systems. More particularly, the presently disclosed subject matter relates to systems and methods for using sensing of real object position, trajectory, and/or attitude to enable user interaction with a virtual object.

BACKGROUND

Augmented reality systems (also referred to as "mixed reality systems") provide users with a view of a physical, real world environment having elements that are augmented by computer-generated or extracted real world input, such as video, sound, or graphics. Computer-generated enhancements are layered atop an existing reality in order to make it more meaningful through the ability to interact with it. Augmented reality has been developed into "apps" for use on mobile computing devices, such as smartphones or tablet computers, to blend digital components into a displayed view of the real world in such a way that they enhance one another. Augmented reality can also be achieved with more immersive hardware, through the use of head-mounted displays (HMDs) that blend the virtual imagery with the real-world view, or through a video that merges virtual objects with a real-time camera captured view of the real environment.

A virtual reality system is another type of system used for enhancing a user's interface with a computing device. Virtual reality is an artificial, computer-generated simulation or recreation of a real life environment or situation. This technology may use HMDs, or employ large monitors and projector-based environments (called world-fixed displays), to generate realistic images, sounds, and/or other sensations that simulate a user's physical presence in a virtual reality environment. Virtual reality systems can replace a real-world environment with a simulated one, whereas an augmented reality system can enhance one's perception of reality.

An important component of augmented reality and virtual reality systems is the user interface. An example user interface is a "wand controller," which can function like a cross between a motion controller and a pen. Such a user interface or wand controller may be elongated in shape for use by a user to "point" to a virtual object in the augmented or virtual reality environment. The system may recognize that the virtual object is being pointed to. Subsequently, the user may depress a button on the wand controller to thereby allow the user to use the "wand" to move or otherwise engage with the object.

Selection and manipulation of virtual objects in world-fixed displays, such as cave automatic virtual environment (CAVE) systems, are limited by the narrow avenue of interaction possibilities provided by wand controllers. Issues, such as occlusion and the lack of realistic haptic feedback caused by such a user interface, hinder the ability to perform realistic interactions. Accordingly, there is a need for improved systems and techniques for allowing users to interact with virtual objects within augmented and virtual reality environments.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein are systems and methods for using sensing of real object position, trajectories, and/or attitude to enable user interaction with a virtual object. According to an aspect, a system can include one or more sensors configured to detect or calculate the boundaries of a transparent, real object within a three-dimensional coordinate system. The system may include a computing device configured to track positions of the detected boundaries of the real object within the three-dimensional coordinate system. The computing device may also track the position and orientation of a virtual object within the three-dimensional coordinate system. The computing device may determine whether the position of the virtual object is within the positions of the detected boundaries of the real object. The computing device may also enable user interaction with the virtual object via user interface and receive input for interacting with the virtual object in response to determining that the position of the virtual object is within the positions of the detected boundaries.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. A brief description of the drawings follows.

DETAILED DESCRIPTION

Figure 1A:
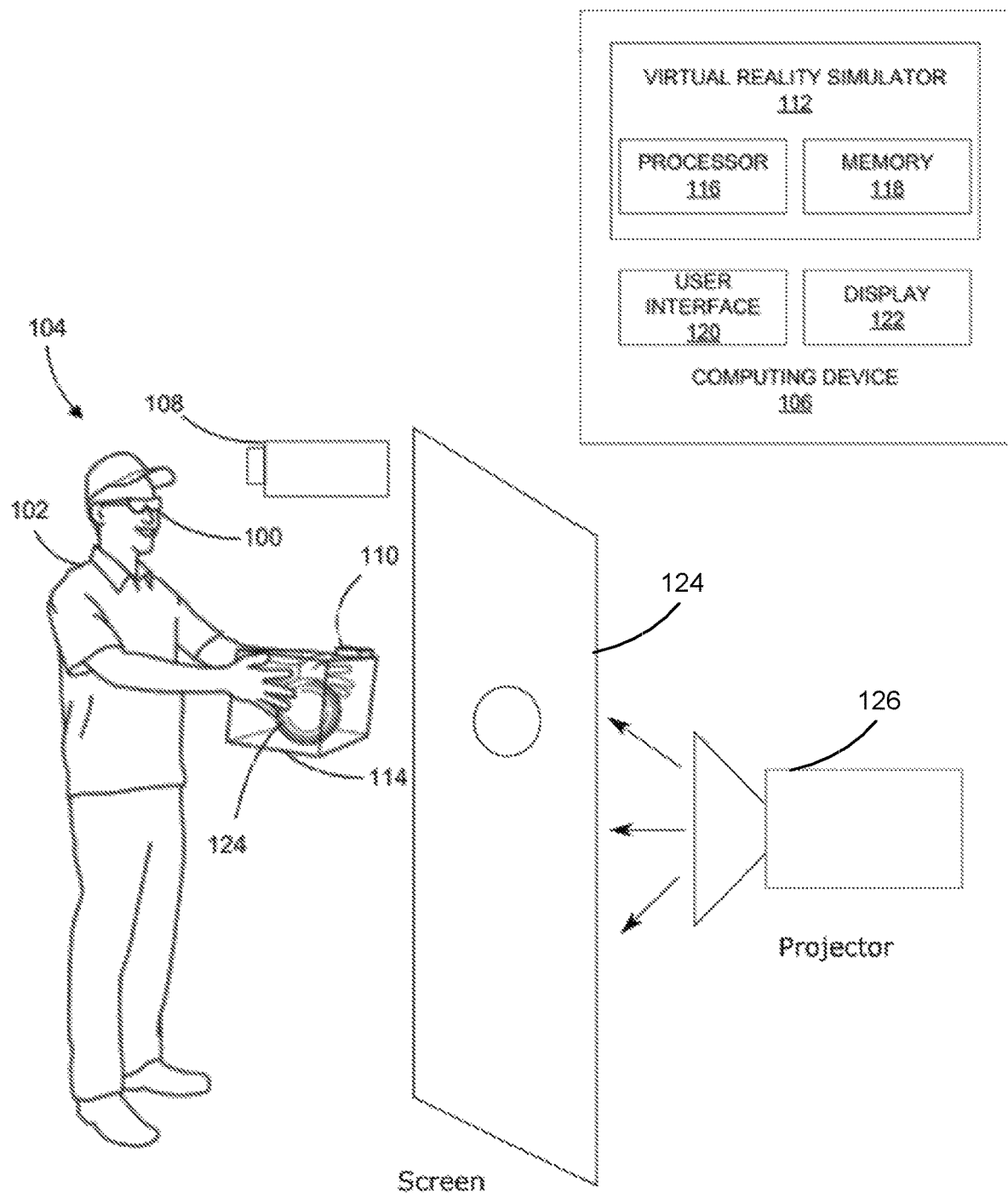
FIG. 1A is a diagram of an example system for using sensing of real object position, trajectory, and/or attitude to enable user interaction with a virtual object in accordance with embodiments of the present disclosure.

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies.

Articles "a" and "an" are used herein to refer to one or to more than one (i.e., at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

As referred to herein, the term "computing device" should be broadly construed. It can include any type of device including hardware, software, firmware, the like, and combinations thereof. A computing device may include one or more processors and memory or other suitable non-transitory, computer readable storage medium having computer readable program code for implementing methods in accordance with embodiments of the present disclosure. A computing device may be, for example, a server. In another example, a computing device may be a mobile computing device such as, for example, but not limited to, a smart phone, a cell phone, a pager, a personal digital assistant (PDA), a mobile computer with a smart phone client, or the like. A computing device can also include any type of conventional computer, for example, a laptop computer or a tablet computer. A typical mobile computing device is a wireless data access-enabled device (e.g., an iPHONE® smart phone, a BLACKBERRY® smart phone, a NEXUS ONE™ smart phone, an iPAD® device, or the like) that is capable of sending and receiving data in a wireless manner using protocols like the Internet Protocol, or IP, and the hypertext transfer protocol, or HTTP. This allows users to access information via wireless devices, such as smart phones, mobile phones, pagers, two-way radios, communicators, and the like. Wireless data access is supported by many wireless networks, including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network). In a representative embodiment, the mobile device is a cellular telephone or smart phone that operates over GPRS (General Packet Radio Services), which is a data technology for GSM networks. In addition to a conventional voice communication, a given mobile device can communicate with another such device via many different types of message transfer techniques, including SMS (short message service), enhanced SMS (EMS), multi-media message (MMS), email, paging, or other known or later-developed wireless data formats.

It is noted that systems for displaying and experiencing virtual content can generally be classified as either world-fixed, such as CAVE systems, or user-fixed, such as with suitable glasses. Systems and methods disclosed herein may be utilized in either world-fixed or user-fixed systems as described herein by example.

Disclosed herein are systems and methods for using sensing of real object position, trajectory, and/or attitude to enable user interaction with a virtual object, which may reside in an augmented or virtual reality environment. In accordance with embodiments, a system may include one or more sensors configured to detect or calculate the boundaries of a substantially or at least partially transparent, real object (sometimes referred to herein as a "specimen box") within a three-dimensional (3D) coordinate system, which may be defined in a virtual reality or augmented reality environment by a suitable computing device. During an example use of the real object to interact with a virtual object, a user may hold the real object, and the virtual object may appear to the user, through use of the virtual reality or augmented reality display, to be positioned within the real object. The user may also move to a different position or change the orientation of the real object to cause the virtual object to change position or orientation in a corresponding way. Thus, the real object can function as a user interface for manipulating the virtual object inside it.

In accordance with embodiments, the virtual object is rendered based on the tracked position and orientation of the real object in relation to the user's point of view, which may be suitably tracked by a computing device. The real object, or specimen box, can provide the weight and tactile feel of an actual object and does not occlude rendered objects in the scene (i.e., the virtual reality environment or augmented reality environment). As a result, for example, the user may see the virtual object as if it exists inside the substantially transparent, or at least partially transparent, real object. The effect of holding a real object can improve user performance and experience within the virtual reality environment or augmented reality environment. To verify this hypothesis, a user study was conducted and is described herein. The user study involved a cognitively loaded inspection task requiring extensive manipulation of a substantially transparent box. Performance of the experimental technique was positively affected by experience with the specimen box.

In an example, the real object used with systems and methods disclosed herein may be shaped as a box. The reasoning for a box form factor is due to its familiarity to a user. In an example, the box-shaped real object may be a cube with outer dimensions of 26.35 centimeters or any other suitable dimensions. The cube may be formed of walls made of transparent material. The walls may define an interior space containing air such that the cube is substantially transparent. The walls may be made of an acrylic or other suitable type of rigid transparent material. In an example, the acrylic wall may be 0.476 centimeters thick or another suitable thickness. To minimize edge effects, the box may be constructed using a type of glue or adhesive that chemically welds the walls together. In a particular example, the walls may be adhered together by use of an SC-94 brand acrylic cement. A cube used in experiments described herein weighed 2,105 grams. A sensor affixed to the cube weighed 36 grams. The total weight of the cube and sensor was therefore 2,141 grams. To preserve the box integrity that could be compromised from the glue off-gassing, a small hole of 5.86 millimeters diameter was drilled near one of the edges.

The cube or other real object may be configured with 6 degrees of freedom (6-DOF) tracking. In an example, an IS-900 wireless head tracking sensor was affixed to the top of the box. In this example, a cable extended from the sensor on the box to a power pack/transmitter that may be clipped onto the belt or pocket of the user. The sensor may be a position sensor or orientation sensor for tracking the position or orientation of the real object. By referencing the tracking sensor values through software, a virtual object can be rendered at an offset from the incoming tracker position, such that the virtual object appears inside the box. In accordance with embodiments, the real object may be tracked with invisible or seamless tracking sensors.

FIG. 1A illustrates a diagram of an example virtual reality system for using positions of detected, real object boundaries to enable user interaction with a virtual object in accordance with embodiments of the present disclosure. Referring to FIG. 1A, the system includes glasses 100 that is being worn by a user 102. The user 102 is located within a world-fixed display environment, generally designated 104, for using the glasses 100 and a computing device 106 to interact with a virtual reality environment. The world-fixed display environment 104 may include various structures or objects that can form a set like stage on which users may move and interact with. The glasses 100 may provide a different image for each eye, enabling the observation of 3D stereoscopic depth by the user. The world-fixed display environment 104 may be a CAVE-type display and include a set of screens 124 (only one of which is shown for ease of depiction) forming a cube-like structure of 2.9 m on its side which displays virtual images generated by projectors 126 (only one of which is shown for ease of depiction) mounted behind the screens. It may also be a different type of world-fixed screen, with projected or otherwise actively generated images (e.g., an LCD monitor).

It is noted that although a rear projector is shown in FIG. 1A, it should be understood that a front projector or other suitable technique may be utilized. For example, the screen may be replaced with a suitable display, such as a large LCD television or tiled wall of displays.

Figure 1B:
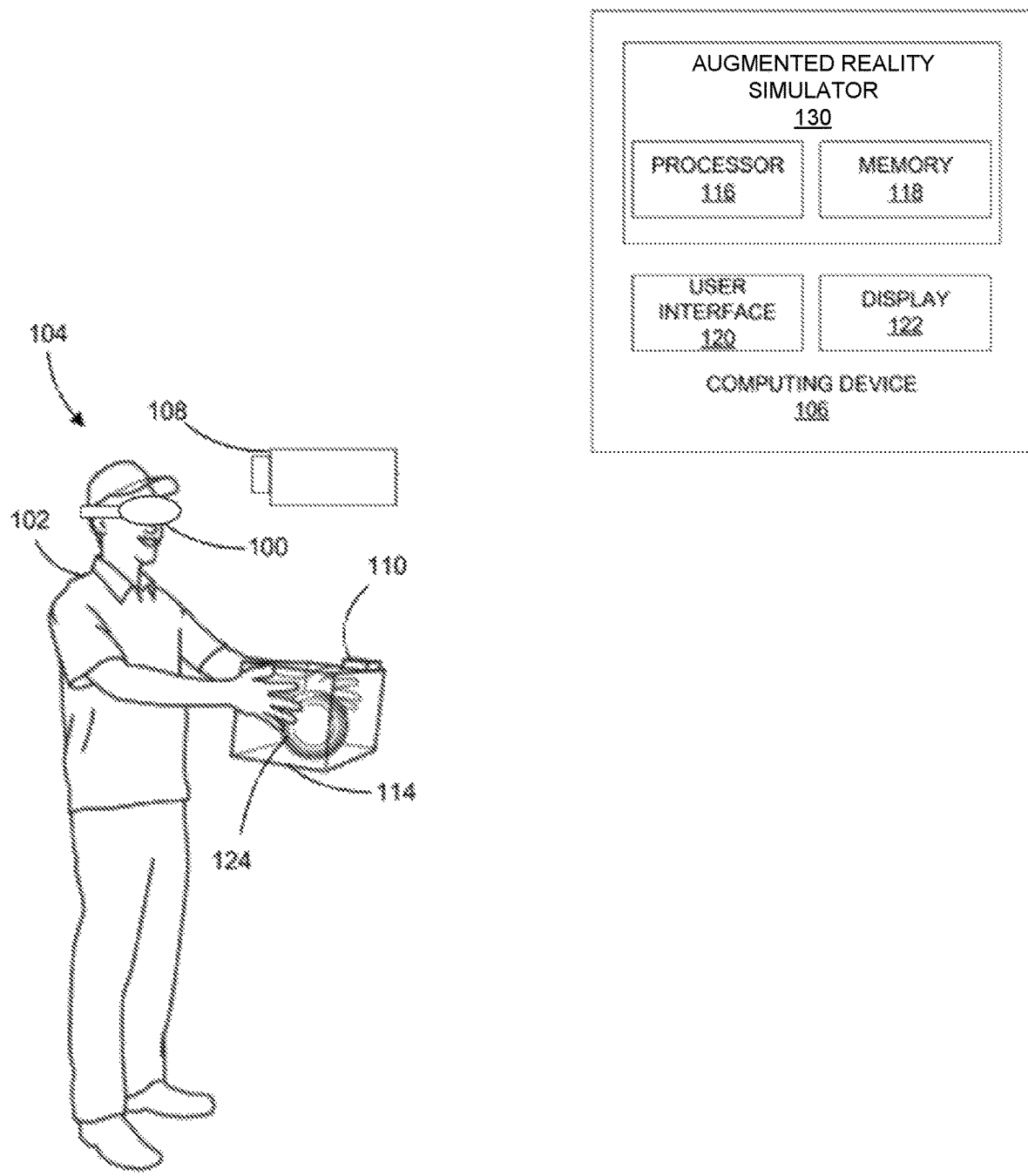
FIG. 1B is a diagram of an example augmented reality system for using positions of detected real world object boundaries to enable user interaction with a virtual object in accordance with embodiments of the present disclosure.

FIG. 1B illustrates a diagram of an example augmented reality system for using positions of detected real world object boundaries to enable user interaction with a virtual object in accordance with embodiments of the present disclosure. Referring to FIG. 1B, the system includes an augmented reality HMD 100 that is being worn by a user. The user is located within a real environment 104 for using the HMD 100 and the computing device 112 to interact with an augmented reality environment. The real environment 104 may include various structures or objects that can form a set and/or stage on which users may move and interact with. The HMD 100 may provide a direct view of the real environment, where virtual imagery can be overlaid, referred to as optical see-through augmented reality. In other embodiments, the HMD 100 may provide low latency images from binocular cameras mounted on the glasses, referred to as video see-through augmented reality.

Figure 1C:
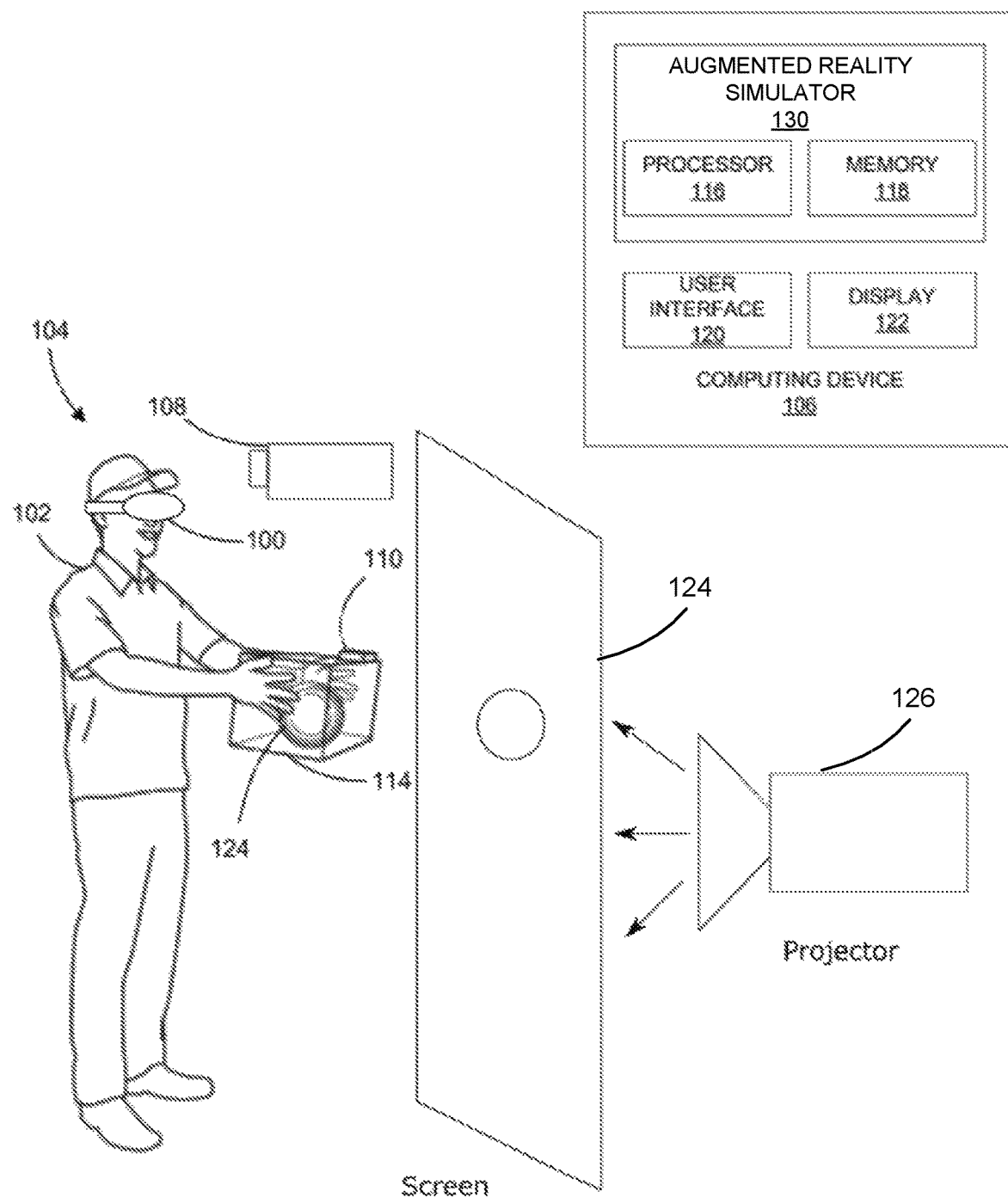
FIG. 1C is a diagram of a configuration that involves both augmented reality and a world-fixed display in accordance with embodiments of the present disclosure

FIG. 1C illustrates a diagram of a configuration that involves both augmented reality and a world-fixed display in accordance with embodiments of the present disclosure. Referring to FIG. 1C, the system includes an augmented-reality optical see-through HMD 100 that also acts as stereoscopic glasses for the world-fixed display. Virtual elements of the scene that are rendered in front of the specimen box (or real object 114) can be rendered by the optical see-through HMD 100 and virtual elements of the scene that are rendered behind the specimen box are rendered by the world-fixed display. In this embodiment, the potential problem of virtual objects occluding or being occluded by the physical box or real object can be eliminated. It is noted that although a rear projector is shown in FIG. 1C, it should be understood that a front projector or other suitable technique may be utilized. For example, the screen may be replaced with a suitable display, such as a large LCD television or tiled wall of displays.

Returning to FIG. 1A, the system includes a position and attitude tracking system 108 for tracking various sensors 110, or markers, located within the real environment 104. The position and attitude tracking system 108 may be embedded in or attached to the glasses 100. Sensors may be placed on the ceiling, floor, or walls of the real environment 104 for use in determining the position and orientation of the glasses 100. The system 108 may include one or more position tracking cameras that can track the sensors 110. The computing device 106 may be operatively connected to the system 108 and a virtual reality simulator 112 may reside on the computing device 106 for suitably generating a virtual reality environment for the user 102. The virtual reality simulator 112 is configured to generate a 3D coordinate system of the virtual reality environment for use in associating positions of real objects in the real environment 104 with virtual objects in the virtual reality environment. In accordance with embodiments, the system may employ video cameras or otherwise unencumbered means to track the specimen box, but without the need for attached sensors on the held real object 114.

In accordance with embodiments, a real object 114 may be held by the user 102 within the real environment 104. One of the sensors 110 may be attached to the real object 114. The sensor 110 attached to the real object may be configured to detect boundaries of the object within the three-dimensional coordinate system generated by the virtual reality simulator. In this example, the real object 114 is cubicle in shape, and the detected boundaries may be the 6 walls that form the outside of the cube. Although the real object 114 is shaped as a cube in this example, it is noted that the real object 114 may be any other suitable shape, such as spherical or tubular. The real object 114 is shown as having a single sensor 110 attached thereto; however, it should be noted that any suitable number of sensors of various types may be attached to the real object 114 for tracking positions of the boundaries and movement of the real object 114. The position and attitude tracking system 108 may be used to track the real object 114 such that other sensors 110 are not needed. This may be achieved through video based feature recognition, or marker detection (often using infrared markers and cameras), where orientation may be spectrally or intensity encoded through the careful placement of markers that preferentially reflect certain wavelengths.

It is noted that one or more sensors or trackers may be situated other than being attached to the real object 114 for tracking positions of the boundaries and movement of the real object 114. In an example, the boundaries and/or movement may be tracked by video-based feature recognition tracking. In another example, tracking may be implemented by retro-reflective infrared (IR) camera tracking. In this example, IR balls may be affixed to the object in order to facilitate tracking.

The virtual reality simulator 112 may be implemented by hardware, software, firmware, or combinations thereof for implementing the functionality described herein. For example, the virtual reality simulator 112 may include one or more processors 116 and memory 118. The virtual reality simulator 112 may track positions of the detected boundaries of the real object 114 within the 3D coordinate system. More particularly, the virtual reality simulator 112 may be communicatively connected to the sensor 110 attached to the real object 114 for tracking positions of the detected boundaries within the 3D coordinate system. It is noted that the computing device 106 may also include a user interface 120 (e.g., a mouse and/or keyboard), display 122, and other hardware components.

The virtual reality simulator 112 is configured to render one or more virtual objects within an augmented reality environment. The augmented reality environment may be mapped by the 3D coordinate system. A position and boundaries of a virtual object within the augmented reality environment may be tracked by the virtual reality simulator 112 in the 3D coordinate system. Referring to FIG. 1A, a virtual object 124 is depicted as a ball. The virtual object 124 may be an overlay displayed to the user 102 by the augmented reality HMD 100 such that the virtual object 124 appears to the user to be within the real environment 104. In the world-fixed display configuration, the image originates on a screen in front of the user. The glasses 100 in that configuration may be simple polarized 3D glasses as those used in 3D movies.

In accordance with embodiments, all of the walls of the real object 114 are made of transparent material and the inside of the real object contains air such that the user 102 can see through the real object 114. In addition, the virtual object 124 may be overlaid in the view of the user 102 with the glasses 100 such that it appears that the virtual object 124 is inside the real object 114. The overlaid virtual object may be rendered by the augmented reality HMD or the world-fixed display, depending on the embodiment. Alternatively, the virtual object 124 may be overlaid in the view of the user 102 with the glasses 100 such that it appears that the virtual object 124 is outside of the real object 114.

The virtual reality simulator 112 may use positions of the detected boundaries of the real object 114 to enable user interaction with the virtual object 124. For example, the virtual reality simulator 112 can track positions of the detected boundaries of the real object 114 within the 3D coordinate system, and also track a position of a virtual object 124 within the 3D coordinate system. The virtual reality simulator 112 may determine whether the position of the virtual object 124 is within the positions of the detected boundaries of the real object 114 in the 3D coordinate system. The virtual reality simulator 112 may enable user interaction with the virtual object 124 in response to determining that the position of the virtual object 124 is within the positions of the detected boundaries of the real object 114. Also, the virtual reality simulator 112 may receive input via the user interface for interacting with the virtual object 124 in response to determining that the position of the virtual object 124 is within the positions of the detected boundaries of the real object 114. Additional details and examples of these functions are described further herein.

Figure 2:
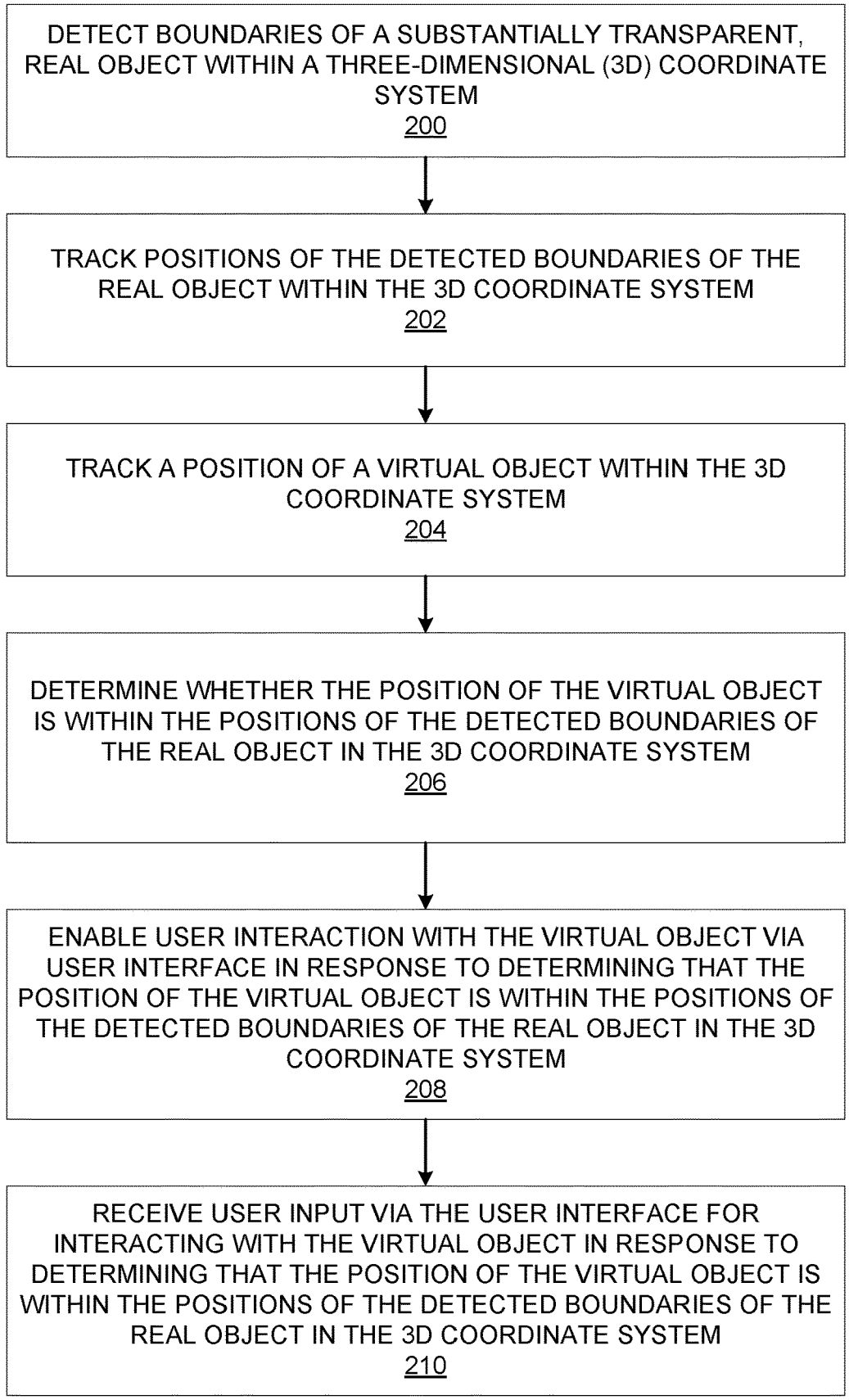
FIG. 2 is a flow diagram of an example method for using positions of detected, real object boundaries to enable user interaction with a virtual object in accordance with embodiments of the present disclosure.

FIG. 2 illustrates a flow diagram of an example method for using positions of detected, real object boundaries to enable user interaction with a virtual object in accordance with embodiments of the present disclosure. FIG. 2 is described in this example as being implemented by the system shown in FIG. 1A, although it should be understood that the method may be implemented by any suitable virtual reality system.

Referring to FIG. 2, the method includes detecting 200 boundaries of a substantially transparent, real object within a 3D coordinate system. For example, the sensor 110 attached to the real object 114 and/or other sensors to detect boundaries of the real object 114 within the 3D coordinate system. The sensor 110 and/or other sensors may be communicatively connected to the computing device 106 for transmitting data about the detected boundaries. Videographic techniques, such as edge detection, can be used to ascertain the boundaries of the object. Motion controllers, which typically employ accelerometers or magnetometers, can be used to ascertain the position and orientation of a reference point of the object. As the reference point is fixed with respect to the boundaries of the box, the geometric relationship between the two can be used to calculate the location of the boundaries given the position and orientation of the reference point. In accordance with embodiment, one point on the real object 114 can be tracked, and by adding an offset (see the example of FIG. 4), the virtual reality simulator 112 can determine the center and other side positions of the real object 114.

The method of FIG. 2 includes tracking 202 positions of the detected boundaries of the real object within the 3D coordinate system. Continuing the aforementioned example, the virtual reality simulator 112 may receive data about the detected boundaries of the real object 114. The virtual reality simulator 112 may suitably store the data in memory, such as memory 118 residing on the computing device 106. Boundaries may alternatively be determined by use of camera based tracking.

With continuing reference to FIG. 2, the method includes tracking 204 a position of a virtual object within the 3D coordinate system. Continuing the aforementioned example, the virtual reality simulator 112 may track a position of the virtual object 124 within the 3D coordinate system. It is noted that boundaries of virtual objects can be represented by a bounding cube, a bounding sphere, or the exact mesh, since the exact vertices that make up the mesh for the virtual object can be known. Each of these representations of boundaries has different trade offs in computing complexity which can affect run time and thus frame per second throughput and responsiveness of the system.

The method of FIG. 2 includes determining 206 whether the position of the virtual object is within the positions of the detected boundaries of the real object in the 3D coordinate system. Continuing the aforementioned example, the virtual reality simulator 112 may determine whether the position of the virtual object 124 is within the positions of the detected boundaries of the real object 114 in the 3D coordinate system.

In accordance with embodiments, the determination of whether the position of a virtual object is within the boundaries of a real object in a 3D coordinate system may be based on a sphere-based collision detection technique. In another example, boundaries may be detected by representing the box as 6 plane equations. For example a plane can be represented as $ax+by+cz+d=0$. By placing in values for a specific xyz position, it can be determined if it is on the plane or above or below. By carefully writing out the plane equations, a point can be checked to see if it matches the criteria of being above all 6 planes (sides of the cube). Thus, the point may be known to be exactly inside the box. To check a virtual object exactly, each vertex of the mesh that makes up the representation of the object can be checked to make sure all points on the object lie inside the box. Modern game engines often provide collision detection/physics support that simplifies these tasks. In this way, the true interaction of the virtual object within the confines of the real object can be simulated (i.e. a rubber ball retains more kinetic energy than a metal ball after colliding with the wall). Using physically valid simulations in conjunction with a rumble pack or other miniature motion system, the specimen box can be used to emulate the tactile sensations associated with interactions of the virtual and real objects (i.e. the virtual metal ball will hit the wall of the specimen box with more force than the rubber ball).

The method of FIG. 2 includes enabling 208 user interaction with the virtual object via a user interface in response to determining that the position of the virtual object is within the positions of the detected boundaries of the real object in the 3D coordinate system. Continuing the aforementioned example, the virtual reality simulator 112 may enable user interaction with the virtual object 124 in response to determining that the position of the virtual object 124 is within the positions of the detected boundaries of the real object 114 in the 3D coordinate system. For example, the virtual object 124 may be stationary at a particular position within a virtual reality environment. The virtual reality simulator 112 may store data indicating the position of the virtual object 114. Further, the user 102 may see the position of the virtual object 114 by use of the glasses 100 and then move the real object 114 such that the virtual object 114 is within the real object 114 as shown in FIG. 1A. In response to determining that the position of the virtual object 114 is within the positions of the detected boundaries of the real object 124, then user interaction with the virtual object 124 may be enabled.

The method of FIG. 2 includes receiving 210 user input via the user interface for interacting with the virtual object in response to determining that the position of the virtual object is within the positions of the detected boundaries of the real object in the 3D coordinate system. Continuing the aforementioned example, once the virtual reality simulator 112 determines that the position of the virtual object 124 is within the positions of the detected boundaries of the real object 112, the user 102 may move and orient the real object 112 to effect the same or similar movement and orientation of the virtual object 124. In this manner, once user interaction with the virtual object 124 is enabled, the user 102 may utilize the real object 114 as a user interface for interacting with the virtual object 124. Further, since the real object 114 is substantially transparent, the user 102 may move the real object 114 in many different positions and orientations and still be able to view the virtual object 124 within the real object 114 regardless of the user's perspective.

In accordance with embodiments, the sensor 110 may be an orientation sensor or position sensor. Further, it is noted that one or more orientation sensors and/or position sensors may be attached to the real object 114 for providing data about its orientation and position. The orientation sensors and position sensors may be communicatively connected to the computing device 106 for sending the collected data to the virtual reality simulator 112. The collected data may be stored in memory 118. The virtual reality simulator 112 may use the collected data for tracking the movement, position, and orientation of the real object 114. In accordance with embodiments, the virtual reality simulator 112 may use the tracked movement, position, and orientation to adjust the movement, position, and orientation of the virtual object 124 such that it matches or corresponds to the real object 114.

In accordance with embodiments, the virtual reality simulator 112 can provide input into the glasses 100 such that the glasses 100 suitably functions in an augmented reality or virtual reality environment. The virtual reality simulator 112 can manage the environment and map it with the three-dimensional coordinate system. The virtual reality simulator 112 may control the glasses 100 or another other suitable display to display real objects and/or virtual objects from a user's perspective within the environment. Displays can be operatively configured within eyeglasses, heads-up displays, and other such equipment. Typically, in augmented reality, images are projected or reflected off an optical element that is worn in an eyeglass or head mount. Augmented reality may include retinal displays that use optical projection systems where the image is scanned directly onto the retina and may perhaps one day be embedded into contact lenses. Typically, in world-fixed displays, images are temporally, spectrally or polarization encoded to represent multiple viewpoints, and the appropriate corresponding type of glasses are worn to achieve the desired stereoscopy. However, autostereoscopic displays such as volumetric or light field displays can eliminate the need for glasses.

Generally, at least 2 different types of displays may be utilized. These are the augmented and world-fixed display cases. In the augmented case, the image can be generated on a plane in front of the user. In the case of the world-fixed display, the glasses may be provided with stereo separation of the images (so that each eye receives a separate image). World-fixed display systems can employ other options for getting separate images to each eye, including autostereo displays or light field displays, which do not require glasses to function.

As described hereinabove, the user 102 may move the real object 114 to effect a movement of the virtual object 124 when the virtual object 124 is within the real object 114 and user interaction is enabled. User interaction with the virtual object 124 may be enabled in response to one or more different predetermined inputs into a user interface. For example, user inputs may include, but are not limited to, a tap input, a shake input, a voice command, the like, or combinations thereof. The real object 114 and/or other devices may be equipped with sensors or various input components to receive such user inputs. As an example, the real object 114 may include an accelerometer for detecting shaking of the real object 114 for effecting control over the virtual object 124.

In accordance with embodiments, user interaction with the virtual object 124 may be disabled by user input. For example, the user 102 may input a command into a user interface for disabling user interaction with the virtual object 124. In an example, the real object 114 may be moved to a position such that the virtual object 124 is not within the real object 114. In this example, the user interaction may be disabled by the virtual reality simulator 112 in response to a tap input, a shake input, voice command, the like, or combinations thereof. The real object 114 may have one or more sensors for detecting such inputs. For example, an accelerometer may be attached to the real object 114 for receipt of such inputs.

Figure 3:
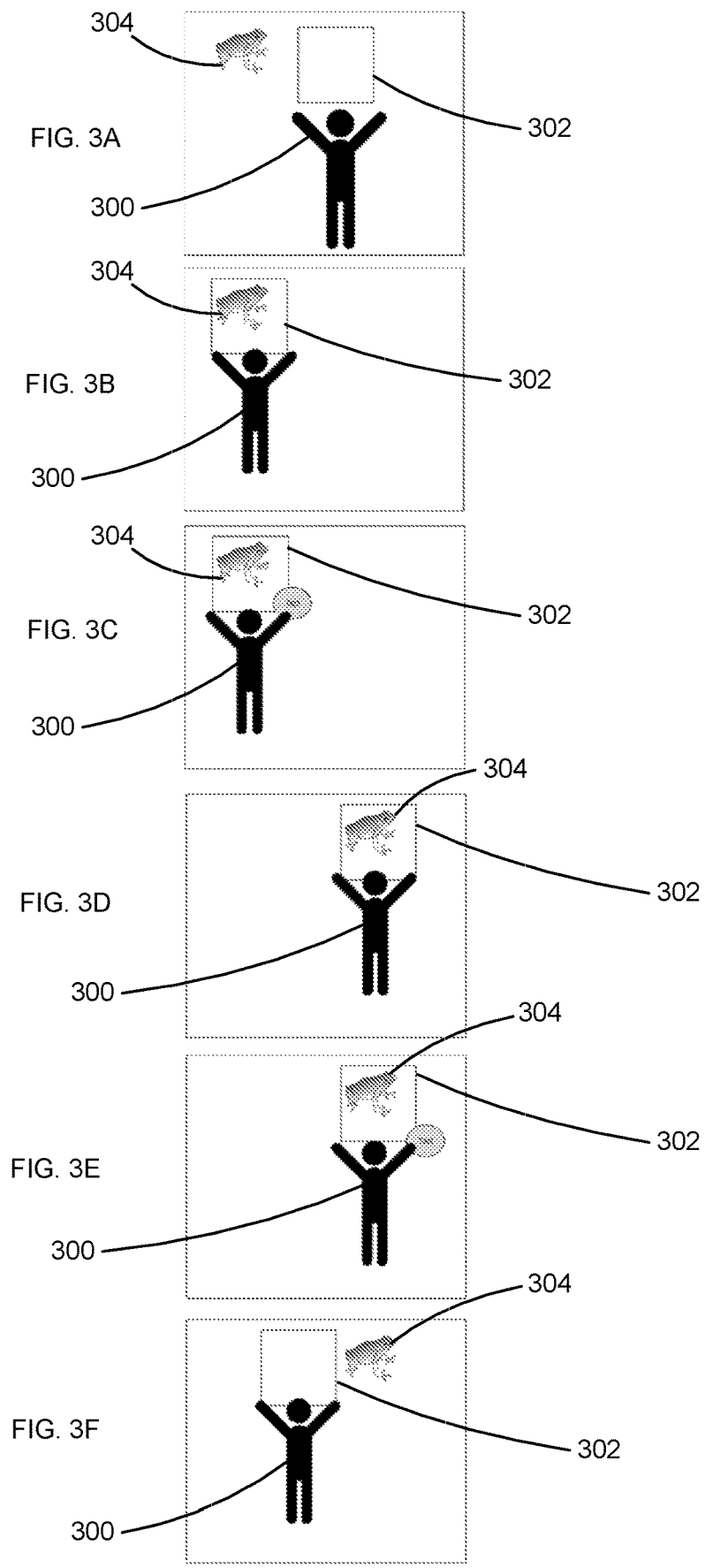
FIGS. 3A-3F are diagrams depicting a user using a real object to enable user interaction with a virtual object in accordance with embodiments of the present disclosure.

FIGS. 3A-3F illustrate diagrams depicting a user 300 using a real object 302 to enable user interaction with a virtual object 304 in accordance with embodiments of the present disclosure. Particularly, the diagrams show a sequence of the user's use of the real object 302 for interacting with the virtual object 304. Referring initially to FIG. 3A, the user 300 is shown holding the real object 302, which is a cube in this example. At this particular time, the virtual object 304, a frog in this example, is outside of the boundaries of the real object 302. Thus, the user 300 cannot use the real object 302 to interact with the virtual object 304 at this particular time. As an example, the virtual reality simulator 112 can use one or more sensors on the real object 302 to determine its boundaries and that the virtual object 304 is outside the boundaries, thus preventing or disabling the interaction.

Now turning to FIG. 3B, this figure shows a subsequent point in time when the user 300 has moved the real object 302 such that the virtual object 304 is within the boundaries of the real object 302. In accordance with embodiments, the virtual reality simulator 112 may determine that the virtual object 304 is within the boundaries of the real object 302. In response to determining that the virtual object 304 is within the boundaries of the real object 302, the virtual reality simulator 112 may enable interaction with the virtual object via user interface.

Subsequently in FIG. 3C, the user 300 is shown tapping the real object 302 for enabling movement and orientation of the virtual object 304 to correspond to the movement and orientation of the real object 302. One or more sensors may detect the tapping and send notification of the tapping to the computing device 106. In response to receipt of the detected tapping notification, the virtual reality simulator 112 may track movement and orientation of the real object 302, and move and orient the virtual object 304 to correspond to the movement and orientation of the real object 302. Alternative to tapping, other examples include shaking the real object 302, a voice command, tapping one's foot, the like, and combinations thereof.

Following FIG. 3C, FIG. 3D shows the virtual object 304 in a different position after the user 302 has moved the real object 302. The virtual object 304 has moved to this position by following movement of the real object 302 to the shown position.

FIG. 3E is subsequent to FIG. 3D and shows the user 300 tapping the real object 302. This second command of tapping the real object 302 can be detected by one or more sensors affixed to the real object 302. The sensor(s) may subsequently send notification of the tapping to the computing device 106. In response to receipt of the detected tapping notification, the virtual reality simulator 112 may disable user interaction with the virtual object 304 such that movement and orientation of the real object 302 does not affect the virtual object 304. Alternative to tapping, other examples include shaking the real object 302, a voice command, tapping one's foot, the like, and combinations thereof. Referring to FIG. 3F, the user 300 has moved the real object 302 such that the virtual object 304 is no longer within the boundaries of the real object 302.

Figure 4:
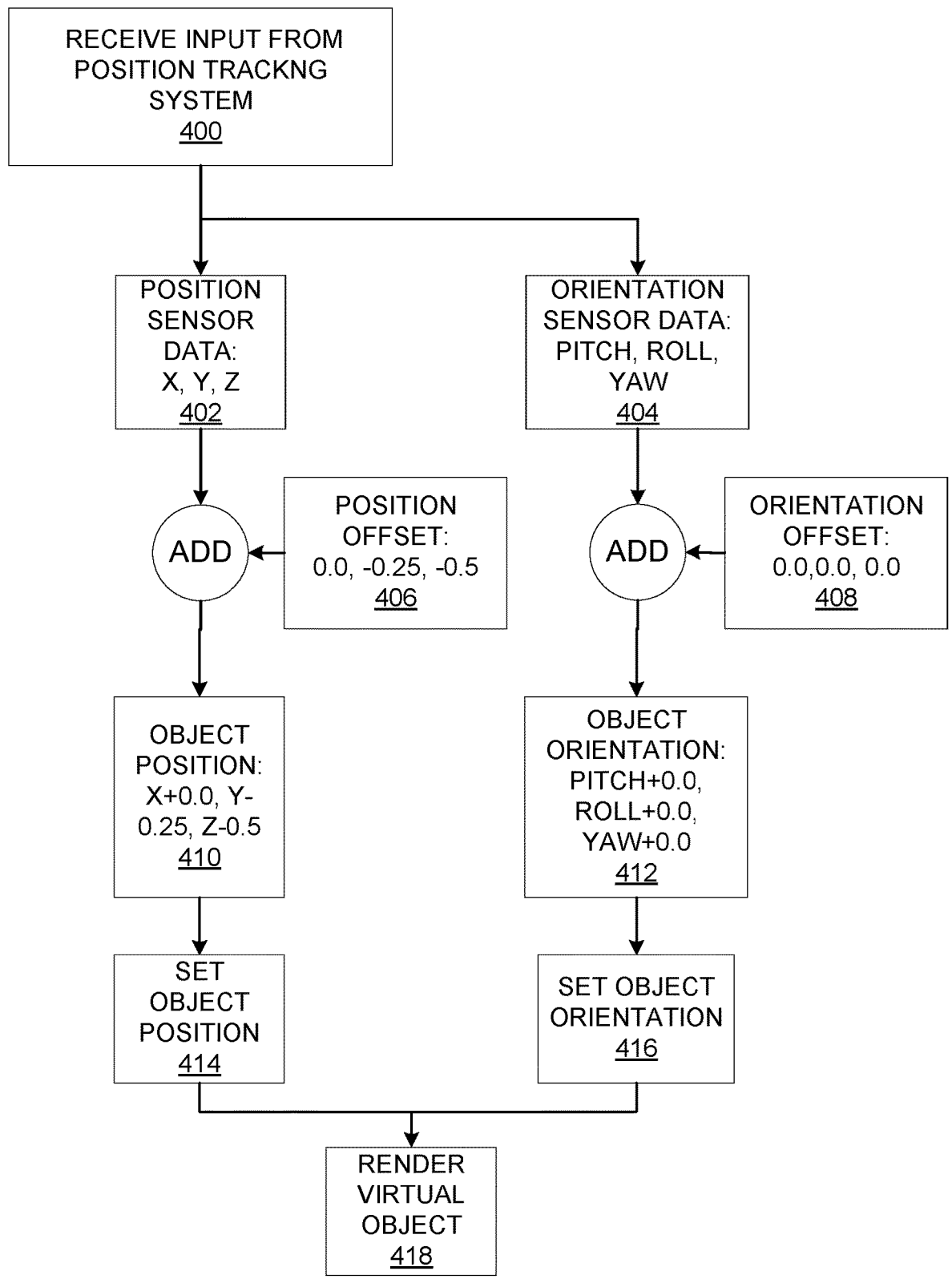
FIG. 4 is a flow diagram of an example method of changing the position and orientation of a virtual object based on movement of a real object in accordance with embodiments of the present disclosure.

FIG. 4 illustrates a flow diagram of an example method of changing the position and orientation of a virtual object based on movement of a real object in accordance with embodiments of the present disclosure. In this example, the method is described as being implemented by the virtual reality simulator 112 of the computing device 106 shown in FIG. 1A, although it should be understood that any suitably configured computing device may implement the method. The method may be used for using position and orientation information about a real object for use in effecting position and orientation changes to a virtual object that the real object is engaged with. The position and orientation information may be used for indicating a real object's position and orientation.

Referring to FIG. 4, the method includes receiving 400 input from a position tracking system. For example, the input may be into the virtual reality simulator 112 and include position sensor data 402 and orientation sensor data 404 for the sensor 110 placed on the real object 114. For example, one or more sensors 110 attached to the real object 114 may detect a position and orientation of the real object 114. This information may be communicated to the virtual reality simulator 112 and stored in memory 118. Also, the information may be collected over time and suitably stored in memory 118. The position information may indicate a position (e.g., x, y, and z coordinates) of the sensor 110 in a 3D coordinate system managed by the virtual reality similar 112. The orientation information may indicate an orientation (e.g., pitch, roll, and yaw) of the sensor 110 in the 3D coordinate system managed by the virtual reality similar 112.

The method of FIG. 4 includes adding the position sensor data 402 with position offset 406 for determining object position of the real object 114. The method also includes adding the orientation sensor data 404 with the orientation offset 408 for determining the orientation of the real object 114. Subsequently, the object position 410 and object orientation 412 may be determined. The virtual reality simulator 112 may set the object position 414 and set the object orientation 416. Subsequently, the virtual reality simulator 112 may render the virtual object 124.

Figure 5:
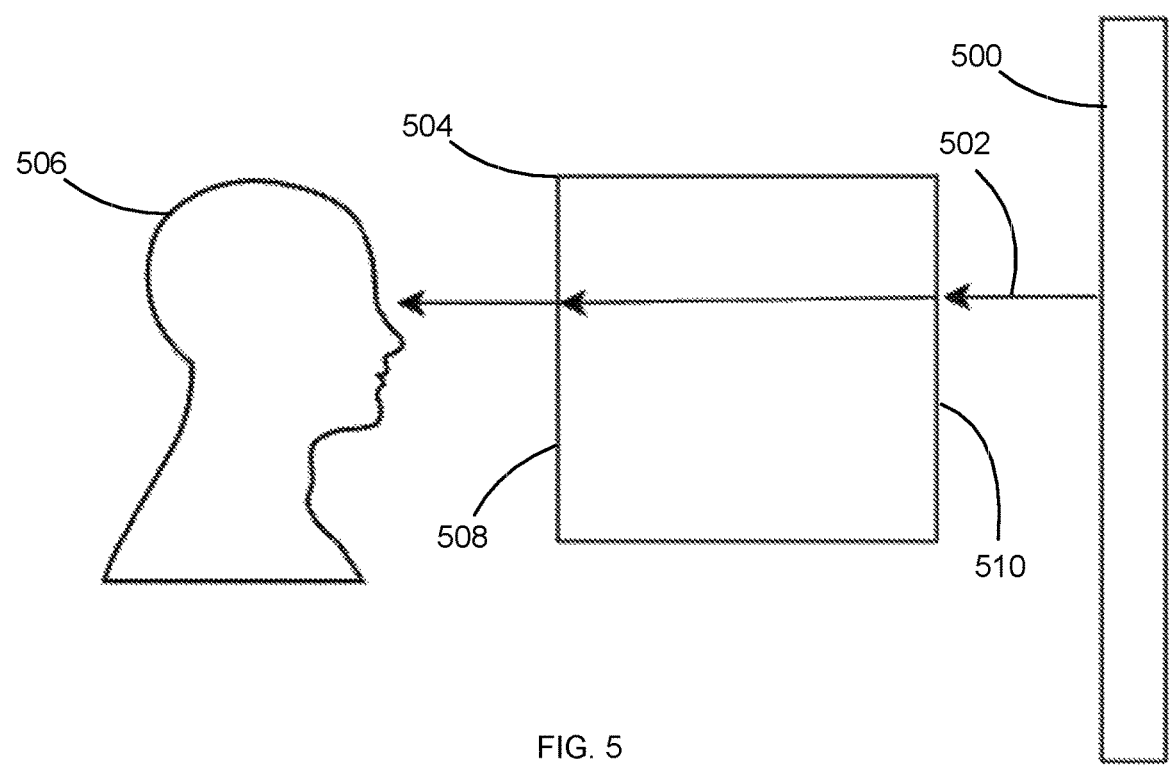
FIG. 5 is a diagram depicting example transmission of light from a display or other source through a real object, and to a user's eyes in accordance with embodiments of the present disclosure.

FIG. 5 illustrates a diagram depicting example transmission of light 502 from a display 500 or other source through a real object 504, as described herein, and to a user's 506 eyes in accordance with embodiments of the present disclosure. This diagram can correspond to the example of FIG. 1A. In this example, the real object 504 is cubical in shape and has walls made of transparent material. The interior of the real object 504 is hollow. Further, the display 500 in this example is a world-fixed display as may be used in CAVE. Referring to FIG. 5, the user can have a good stereo sense of content inside the box as light 500 properly originate from display 500 and transmit through the closest side of the real object 504. Any occlusions from edges are correct, as if the light 502 were emanating from an object inside the real object 504. For virtual objects (e.g., virtual object 124 shown in FIG. 1A) positioned behind the box, the light 502 can be mostly correct from the user's 506 perspective, as in the light 502 would transmit through both sides 508 and 510 to reach the user's eyes 506.

Figure 6:
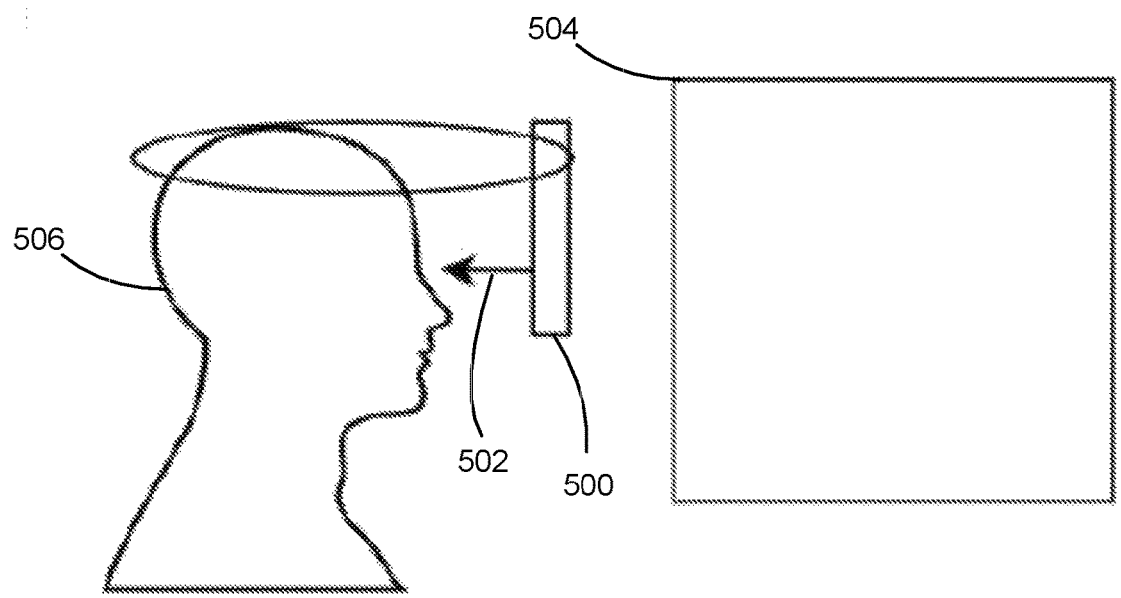
FIG. 6 is a diagram depicting an example transmission of light from an augmented reality display in close proximity to the user's face along with a real object in accordance with embodiments of the present disclosure.

FIG. 6 illustrates a diagram depicting an example transmission of light 502 from a display 500 in close proximity to the user's 506 face along with a real object 504 in accordance with embodiments of the present disclosure. This diagram can correspond to the example of FIG. 1B. In this example, the display 500 may be part of an augmented reality HMD or other display system in which the display 500 is in close proximity to the user 506. Referring to FIG. 6, the diagram presents an augmented reality case in which the image is displayed on a plane in front of the user's 506 eyes.

Figure 7:
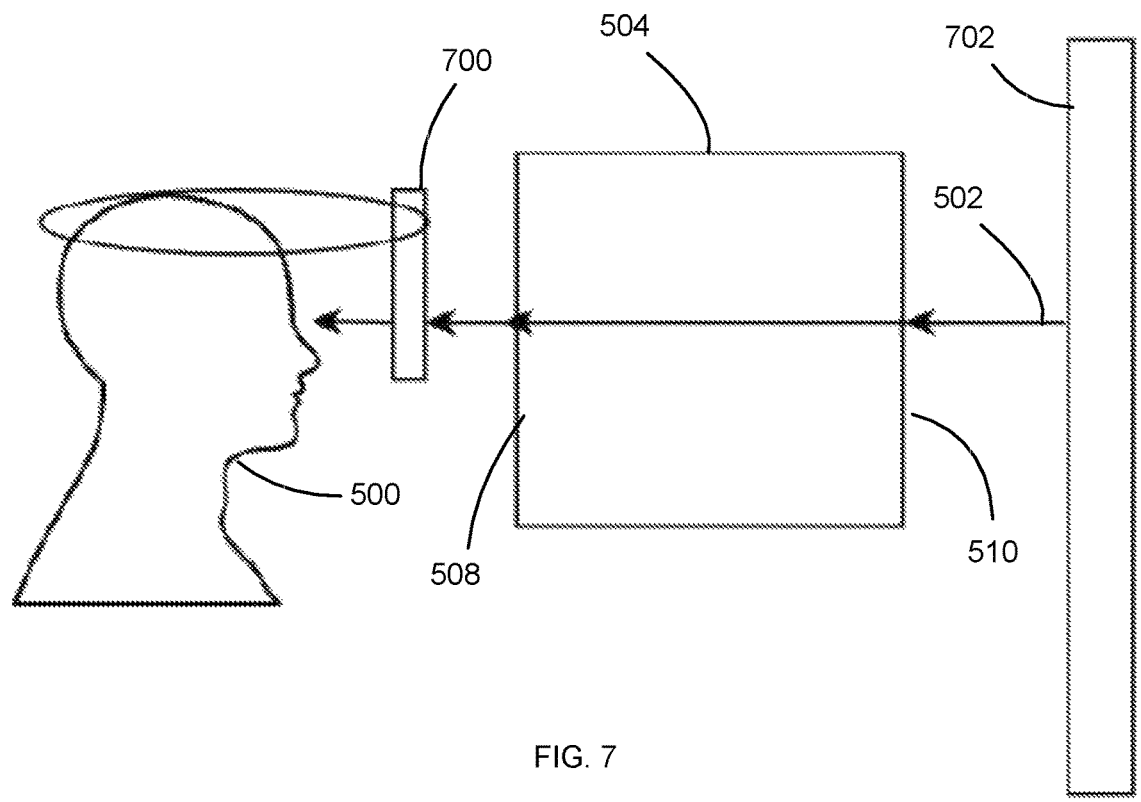
FIG. 7 is a diagram showing use of an augmented reality display in combination with a world fixed display in accordance with embodiments of the present disclosure.

FIG. 7 illustrates a diagram showing use of an augmented reality display 700 in combination with a world-fixed display 702 in accordance with embodiments of the present disclosure. This diagram can correspond to the example of FIG. 1C. Referring to FIG. 7, this system can allow virtual object correctness/artifacts inside the real object 504 (1/2, behind side 508 or in front of side 510); between real object 504 and user 500 (2/2, in front of sides 508 and 510) by displaying the object in the augmented reality display 700); and behind the real object 504 (2/2) by displaying on the world-fixed display 702.

Figure 8:
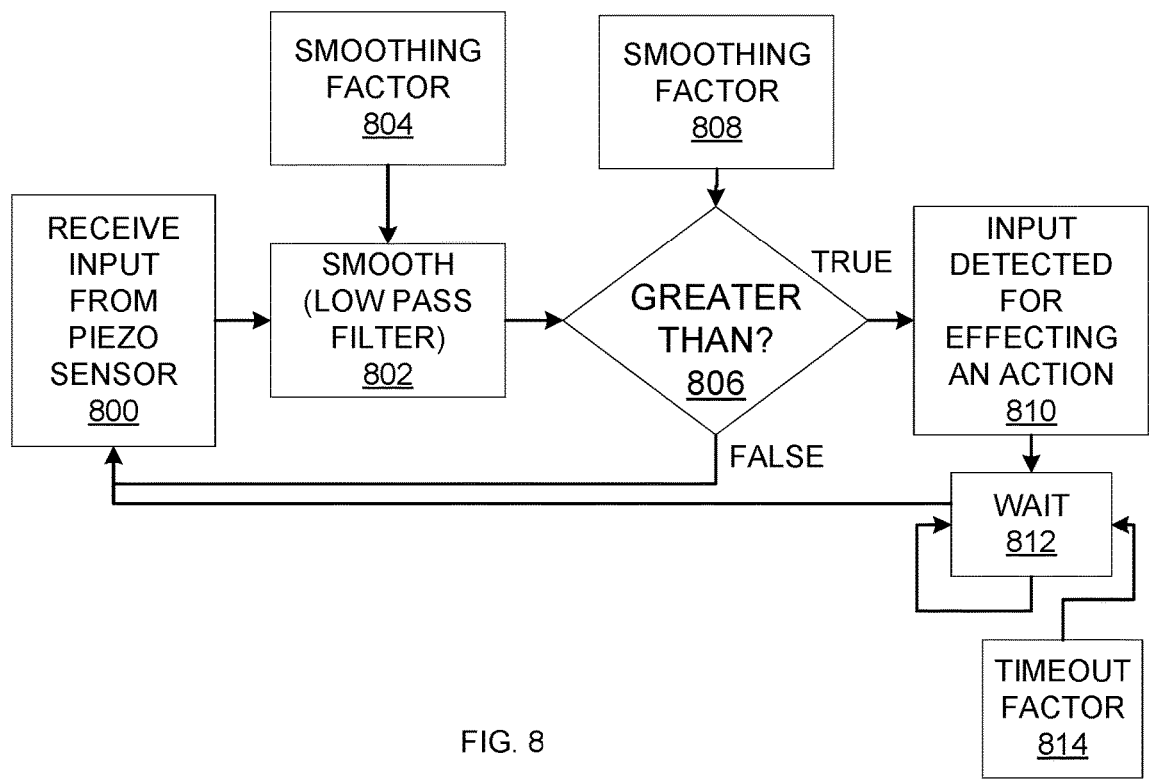
FIG. 8 is a flow diagram of an example method for tap input detection in accordance with embodiments of the present disclosure.

FIG. 8 illustrates a flow diagram of an example method for tap input detection in accordance with embodiments of the present disclosure. This method may be used by, for example, the virtual reality simulator 112 shown in FIG. 1A for detecting a shake input to the real object 114 for interaction with the virtual object 124. For example, the user 102 may position the real object 114 such that the virtual object 124 is positioned within the real object 114. Subsequently and while the virtual object 124 is still within the real object 114, the user 102 may use his or her hand to tap the real object 114. This input may be detected by the sensor 110 and the detected input transmitted to the virtual reality simulator 112. In response to the detection, the virtual reality simulator 112 may track the positioning and orientation of the real object 114 and control the position and orientation of the virtual object 124 such that it matches the real object 114.

In the example of FIG. 8, the method is described as being implemented by the virtual reality simulator 112, but it should be understood that the method may be implemented by another suitably configured computing device. Now referring to FIG. 8, the method includes receiving 800 input from a piezoelectric sensor. For example, the sensor 110 shown in FIG. 1A may be a piezoelectric sensor configured to detect changes in pressure, acceleration, strain, or force by converting them to an electrical signal. The signal may be suitably communicated to the computing device 106 for receipt by the virtual reality simulator 112. The virtual reality simulator 112 may thereby receive the input. The virtual reality simulator 112 may subsequently smooth 802 the received electrical signal with a low pass filter based on a smoothing factor 804, such as 0.1.

The method of FIG. 8 includes determining 806 whether the resulting smoothed signal is greater than a predetermined threshold 808. The predetermined threshold may be, for example, 0.25 or another suitable threshold. In response to determining that the smoothed signal is greater than the predetermined threshold 808, the method may proceed to step 810. As a further example, the virtual reality simulator 112 may receive a stream of numbers (e.g., −1.0 to 1.0). A low pass filter may be applied to the stream of numbers to search for a sample that is over a predetermined threshold. In response to determining that the smoothed signal is not greater than the predetermined threshold 808, the method may return to step 800 to continue receiving input from the sensor.

At step 810 of FIG. 8, the method includes detecting an input intended to effect an action. For example, the virtual reality simulator 112 may determine that an input intended to effect an action has been detected. The virtual reality simulator may subsequently effect the action, such as enablement of the user to move the real object 114 to effect movement of the virtual object 124 in accordance with examples described herein.

The method of FIG. 8 may also include waiting 812 for a timeout factor 814. Continuing the aforementioned example, subsequent to detection of the input at step 810, the virtual reality simulator 112 may wait a predetermined time period prior to returning to step 800. The wait period is intended to prevent double triggering based on the same tap input.

Figure 9:
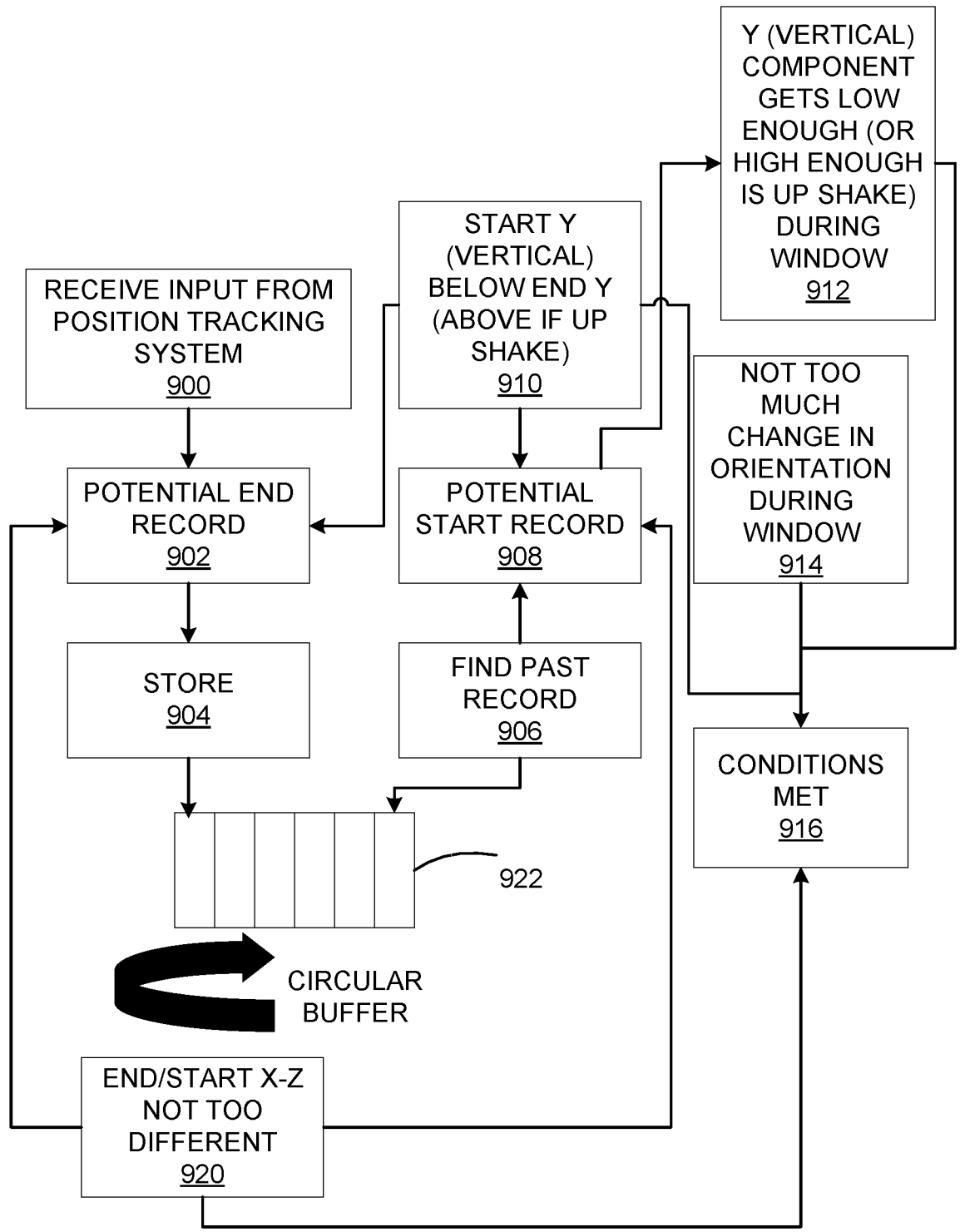
FIG. 9 is a flow diagram of an example method for shake input detection in accordance with embodiments of the present disclosure.

FIG. 9 illustrates a flow diagram of an example method for shake input detection in accordance with embodiments of the present disclosure. This method may be used by, for example, the virtual reality simulator 112 shown in FIG. 1A for detecting a shake input to the real object 114 for interaction with the virtual object 124. For example, the user 102 may position the real object 114 such that the virtual object 124 is positioned within the real object 114. Subsequently and while the virtual object 124 is still within the real object 114, the user 102 may use his or her hand to shake the real object 114. This input may be detected by the sensor 110 and the detected input transmitted to the virtual reality simulator 112. In response to the detection, the virtual reality simulator 112 may track the positioning and orientation of the real object 114 and control the position and orientation of the virtual object 124 such that it matches the real object 114.

In the example of FIG. 9, the method is described as being implemented by the virtual reality simulator 112, but it should be understood that the method may be implemented by another suitably configured computing device. Now referring to FIG. 9, the method includes receiving input for the system 108. Step 900 includes providing the tracking of the real object (such as by sensor 110) and adjusting (applying offsets) to obtain the proper center of the box as discussed in the example of FIG. 6. Step 902 includes packaging the information in a suitable package for electronic storage (position and orientation of box and current time). Step 904 includes storing the box state in a circular buffer 922.

Step 906 of FIG. 9 includes determining the record in A history list that is a predetermined time in the past. For example, check the box position and orientation 800 ms in the past. Step 908 includes setting the start record (if a suitable record was found in step 906). Step 910 includes examining the start record to determine whether the start y (height off the ground) is below the ending y (or height off the ground). Data is filled in the circular buffer 922 from left to right. When arriving at the right of the buffer 922, the index is updated back to the 0 entry (leftmost entry), thus overwriting past data. Useful when we have a certain amount of history we want to store, and continuously update. Commonly used in computer science algorithms.

At step 920 of FIG. 9, a comparison of the XZ of the start box position and end box position is conducted to make sure there was not too much movement in the XZ plane. At step 912, there is a determination that at some time point between present and the past (determined in 906/908), a certain distance below the start position is reached. This threshold shows how far the user has to go down to trigger the event. Step 914 includes examining the orientation of the object to make sure that during the times between start and end there is not too much orientation (rotational change) of the object. At step 916 of FIG. 9, there is a check of whether all 4 conditions are met. If all 4 conditions are met, it is determined that a shake interaction was input by the user.

Figure 10:
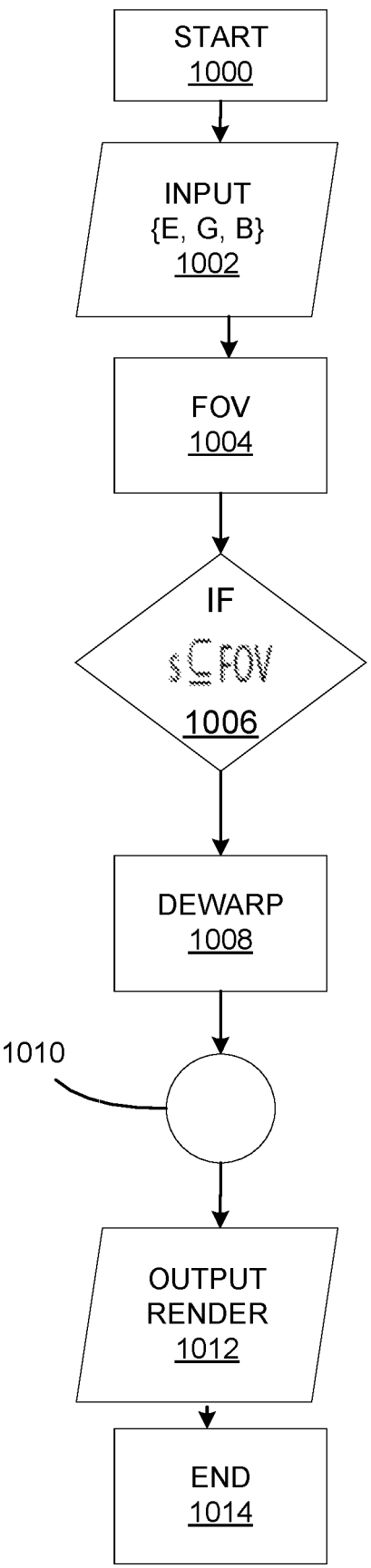
FIG. 10 illustrates a flow diagram of an example method of dewarping in accordance with embodiments of the present disclosure.

FIG. 10 illustrates a flow diagram of an example method of dewarping in accordance with embodiments of the present disclosure. This example method is described as being implemented by the virtual reality simulator 112 of the computing device 106, although it is noted that the method may be implemented by any suitably configured computing device. Referring to FIG. 10, the eye position (E), gaze direction (G), and box position (B) are used to calculate the operator field of view (FOV). The FOV is mapped to the corresponding screen position. Only the regions within the FOV of the specimen box are dewarped. Concerning the sphere concept, ray tracing of a scale model of a 10 inch diameter thin walled sphere indicate that the aberrations are small and likely imperceptible, but the magnification and distortion could be corrected with dewarping to improve perception. This can be achieved through a calibration dictionary that's done on the front end to significantly reduce computation (i.e., no need for real-time ray tracing), but real-time information about the box position, eye position, and gaze are needed to calculate the FOV, and then dewarp the appropriate portion of the screen using the dictionary. Concerning the box, the normal incidence case is trivial, as most will not hold specimen box at head level. Instead, they hold objects at the level of the mid-abdomen. Also, given the interactive component of the specimen box, the user will frequently reorient to appreciate the object rendered inside. For this reason, most of the time, other angles of incidence will be prominent. In this case, there is a small translation of the object position. This too can be compensated in a similar fashion. Although we need a dictionary of calibrations to cover all of the space of {E,G,B}, only a 2D correction of the images on the world-fixed display is needed similar to the technique used in "Handheld, rapidly switchable, anterior/posterior segment swept source optical coherence tomography probe" by Nankivil, Derek, et al. Biomedical Optics Express 6.11 (2015): 4516-4528.

The presently disclosed systems and methods may be implemented in any suitable environment and with any suitable equipment. For example, the system may be implemented in a six-sided CAVE-type environment. Tracking may be provided, for example, via an Intersense IS-900 tracking system available from Thales Visionix, Inc. of Millerica, Mass. Each wall of the CAVE may have two Christie Digital WU7K-M projectors running at 120 Hz. The projectors may be overlapped and blended, and provide a total resolution of 1920×1920 pixels per wall. Active stereo may be achieved via Volfoni EDGE™ RF liquid crystal shutter glasses. The simulation may be run at 120 Hz active stereo—effectively 60 frames per second (fps).

For the software run on a computing device, the Unity 5.3 with the MiddleVR plugin may be used to support clustered CAVE-type renderings. The scripts to control various aspects of the simulation inside Unity may be written in C#. Logs can be written out to disk in the form of CSV files, and later combined via a helper program into one large CSV file (containing all of the users) that can be loaded into IBM SPSS statistical software.

Described herein is use of a cubical-shaped real object for use in accordance with embodiments of the present disclosure. It should be understood that the substantially transparent, or at least partially transparent, real object may alternatively be a variety of other shapes, sizes, weights, and other characteristics. In an example, the real object may have a weight set for matching the assumed weight of a virtual object inside it. Such weight matching may be useful, for example, for an ecologically valid skills training session where the user has to manipulate different objects with varying weights. Multiple boxes with varying weights may be available to the user, and the appropriate box may be selected to match the weight of the virtual object.

In accordance with embodiments, the real object may be spherical in shape. A spherically shaped real object may be used in complementary situations to a cubical shaped real object.

In accordance with embodiments, a system may determine whether the position of a virtual object with respect to positions of detected boundaries of a real object meet a predetermined criteria. In response to determining that the position of the virtual object with respect to the positions of the detected boundaries of the real object meet the predetermined criteria, the system may enable user interaction with the virtual object via user interface; and receive input via the user interface for interacting with the virtual object. As an example, the virtual reality simulator 112 shown in FIG. 1A may determine whether the position of the virtual object 124 with respect to positions of detected boundaries of the real object 114 meet a predetermined criteria. For example, the virtual object 124 may be positioned on an upper surface of the real object 114. The virtual reality simulator 112 may recognize that the virtual object 124 is at this position or another predetermined position and/or orientation with respect to the real object 114. In response to determining that the virtual object 124 is on top of the upper surface of the real object 114 or at some other predetermined position and/or orientation, the virtual reality simulator 112 may enable user interaction with the virtual object 124 via a user interface, and receipt of input via the user interface for interacting with the virtual object 124.

In the embodiments of determining that the position of the virtual object with respect to the positions of the detected boundaries of the real object meet the predetermined criteria, the simulator may recognize that the virtual object is positioned on a top surface of the real object (i.e., the top surface of a box held by the user). In this example, the virtual object can be a ball that reacts as a real ball would when on top of a moveable surface. Tilting of the surface of the real object can be detected, and the virtual ball can react as it would in the real world by rolling down the slope of the top surface. By tilting the other way, the virtual ball can roll in the opposite direction. In this way, a user can move the real object to balance the virtual ball on top of the box. Such a configuration can be useful for balance training, physical rehabilitation, and other interactions that benefit from manipulating the physical weight of the box while balancing. In another example, the top surface can have a very slightly concave surface. In this example, a user can maneuver a ball balanced on the top surface that is simulated to have convexity. The convexity or other shape of the top surface can be adjusted by the simulator. In this way, the ball can be maneuvered (simulated by the box/VR) through a course (simulated by a treadmill-like moving track in the virtual reality environment) for improving the user's strength and range of motion. In addition, the course can be adjusted to suit the user. In this way, it can be customized to progress in intensity and complexity as a patient recovers. Also, such configurations may be used in computer gaming applications.

Computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:
1. A system comprising:
   at least one of a position sensor or tracker configured to detect boundaries of at least a partially transparent, real object within a three-dimensional coordinate system; and
   a computing device configured to:

track positions of the detected boundaries of the real object within the three-dimensional coordinate system;

control a position of a virtual object within the three-dimensional coordinate system;

determine whether the position of the virtual object is within the positions of the detected boundaries of the real object in the three-dimensional coordinate system; and in response to determining that the position of the virtual object is within the positions of the detected boundaries of the real object:

enable user interaction with the virtual object via user interface; and receive input via the user interface for interacting with the virtual object.

2. The system of claim 1, wherein the at least one position sensor or tracker is configured to detect a position of the real object within the three-dimensional coordinate system, and wherein the computing device is communicatively connected to the at least one position sensor or tracker for receipt of the detected position of the real object.

3. The system of claim 1, further comprising at least one orientation sensor or tracker configured to detect an orientation of the real object within the three-dimensional coordinate system, and wherein the computing device is configured to:

track the detected orientation of the real object within the three-dimensional coordinate system; and in response to determining that the position of the virtual object is within the positions of the detected boundaries of the real object, orient the virtual object to correspond to the detected orientation of the real object.

4. The system of claim 1, wherein the computing device is configured to:

track movement of the real object based on the tracked positions of the detected boundaries of the real object; and in response to determining that the position of the virtual object is within the positions of the detected boundaries of the real object, move the virtual object to correspond to the tracked movement of the real object.

5. The system of claim 1, further comprising one or more rumble packs and/or one or more motion systems that are attached to the real object and used in conjunction with physics simulations to provide an ecologically valid simulation of the interaction of the virtual object with the real object.

6. The system of claim 1, further comprising a display, and wherein the computing device is operatively connected to the display and configured to control the display to display the virtual object at their respective positions within the three-dimensional coordinate system.

7. The system of claim 6, wherein the computing device is configured to:

manage an augmented reality environment that is mapped by the three-dimensional coordinate system; and control the display such that the virtual object and real object are seen from a user's perspective within the augmented reality environment.

8. The system of claim 7, wherein the display is operatively configured within a world-fixed display, and wherein the system further comprises:

one of a plurality of projectors or a plurality of monitors configured to render the virtual reality environment; and the user wears stereoscopic glasses, or the display is autostereoscopic.

9. The system of claim 1, wherein the computing device is configured to disable user interaction with the virtual object via the user interface.

10. The system of claim 9, wherein the computing device is configured to disable the user interaction in response to receipt of a predetermined input into the user interface.

11. The system of claim 10, wherein the predetermined input comprises one of a tap input, a shake input, and a voice command.

12. The system of claim 1, further comprising one of a display or projector configured to project the virtual object onto a surface for view by the user, and wherein the computing device control the display or projector to display the virtual object on the surface at a position such that the virtual object appears within the positions of the detected boundaries of the real object.

13. The system of claim 1, wherein the at least one position sensor or tracker is attached to or remote from the real object.

14. The system of claim 1, wherein the real object is cuboid or spherical in shape.

15. The system of claim 1, wherein the real object comprises walls made of transparent material, and wherein the walls define an interior space containing air, other gases, or vacuum.

16. The system of claim 1, wherein the computing device is configured to enable the user interaction in response to receipt of a predetermined input into the user interface.

17. The system of claim 16, wherein the predetermined input comprises one of a tap input, a shake input, and a voice command.

18. The system of claim 16, wherein the predetermined input comprises one of a tap input to the real object and a shake input to the real object.

19. The system of claim 1, wherein refractive distortions due to transparent material of the real object are corrected using real-time dewarping.

20. A method comprising:

using at least one position sensor to detect boundaries of at least a partially transparent, real object within a three-dimensional coordinate system; and tracking positions of the detected boundaries of the real object within the three-dimensional coordinate system;

tracking a position of a virtual object within the three-dimensional coordinate system;

determining whether the position of the virtual object is within the positions of the detected boundaries of the real object in the three-dimensional coordinate system; and in response to determining that the position of the virtual object is within the positions of the detected boundaries of the real object:

enabling user interaction with the virtual object via user interface; and receiving input via the user interface for interacting with the virtual object.

21. The method of claim 20, wherein the at least one sensor is attached to the real object.

22. The method of claim 20, further comprising:

using at least one orientation sensor to detect an orientation of the real object within the three-dimensional coordinate system;

tracking the detected orientation of the real object within the three-dimensional coordinate system; and orienting the virtual object to correspond to the detected orientation of the real object in response to determining that the position of the virtual object is within the positions of the detected boundaries of the real object.

23. The method of claim 20, further comprising:

tracking movement of the real object based on the tracked positions of the detected boundaries of the real object; and moving the virtual object to correspond to the tracked movement of the real object in response to determining that the position of the virtual object is within the positions of the detected boundaries of the real object.

24. The method of claim 20, further comprising using a display to display the virtual object at their respective positions within the three-dimensional coordinate system.

25. The method of claim 24, further comprising:

managing an augmented reality environment that is mapped by the three-dimensional coordinate system; and controlling the display to display the real object and the virtual object from a user's perspective within the augmented reality environment.

26. The method of claim 25, wherein the display is operatively configured within a world-fixed display, wherein the user wears stereoscopic glasses or the display is autostereoscopic, and wherein the method comprising rendering the virtual reality environment using one of a plurality of projectors or a plurality of monitors.

27. The method of claim 20, further comprising enabling the user interaction in response to receipt of a predetermined input into the user interface.

28. The method of claim 27, wherein the predetermined input comprises one of a tap input, a shake input, and a voice command.

29. The method of claim 27, wherein the predetermined input comprises one of a tap input to the real object and a shake input to the real object.

30. The method of claim 20, further comprising disabling user interaction with the virtual object via the user interface.

31. The method of claim 30, further comprising disabling the user interaction in response to receipt of a predetermined input into the user interface.

32. The method of claim 31, wherein the predetermined input comprises one of a tap input, a shake input, and a voice command.

33. The method of claim 20, further comprising:

using one of a display or projector to project the virtual object onto a surface for view by the user; and controlling the display or projector to display the virtual object on the surface at a position such that the virtual object appears within the positions of the detected boundaries of the real object.

34. The method of claim 20, further comprising using the at least one of position sensor and tracker to detect a position of the real object within the three-dimensional coordinate system.

35. The method of claim 20, wherein the real object is cuboid in shape.

36. The method of claim 20, wherein the real object comprises walls made of transparent material, and wherein the walls define an interior space containing air, gas, or vacuum.

37. A system comprising:

at least one of a position sensor or tracker configured to detect boundaries of at least a partially transparent, real object within a three-dimensional coordinate system; and a computing device configured to:

track positions of the detected boundaries of the real object within the three-dimensional coordinate system;

control a position of a virtual object within the three-dimensional coordinate system;

determine whether the position of the virtual object is within the positions of the detected boundaries of the real object in the three-dimensional coordinate system; and in response to determining that the position of the virtual object with respect to the positions of the detected boundaries of the real object meet the predetermined criteria:

enable user interaction with the virtual object via user interface; and receive input via the user interface for interacting with the virtual object.

38. The system of claim 37, wherein the real object is cuboid in shape, and wherein the computing device is configured to:

determine that the virtual object is positioned on a top surface of the real object;

in response to determining that the virtual object is positioned on the top surface of the real object:

enable the user interaction with the virtual object via user interface; and receive the input via the user interface for interacting with the virtual object.

39. The method of claim 37, wherein the real object is cuboid in shape, and wherein the computing device is configured to:

determine that the virtual object is positioned on a top surface of the real object;

in response to determining that the virtual object is positioned on the top surface of the real object:

enabling the user interaction with the virtual object via user interface; and receiving the input via the user interface for interacting with the virtual object.

40. A method comprising:

using at least one position sensor to detect boundaries of at least a partially transparent, real object within a three-dimensional coordinate system; and tracking positions of the detected boundaries of the real object within the three-dimensional coordinate system;

tracking a position of a virtual object within the three-dimensional coordinate system;

determining whether the position of the virtual object is within the positions of the detected boundaries of the real object in the three-dimensional coordinate system; and in response to determining that the position of the virtual object is within the positions of the detected boundaries of the real object:

enabling user interaction with the virtual object via user interface; and receiving input via the user interface for interacting with the virtual object.

* * * * *